United States Patent [19]

Fischer

[11] Patent Number: 4,803,979

[45] Date of Patent: Feb. 14, 1989

[54] PULSATING WATER AND AIR JET STRUCTURE FOR CLEANING HELMET WINDOW

[76] Inventor: Edmund C. Fischer, 5918 Southern Hills Dr., Houston, Tex. 77069

[21] Appl. No.: 54,804

[22] Filed: May 27, 1987

[51] Int. Cl.[4] ........................ A61M 15/00; B08B 3/02

[52] U.S. Cl. .................................. 128/201.15; 2/438; 134/102; 134/172; 134/199

[58] Field of Search ............... 134/102, 172, 198, 199; 2/8, 438; 128/200.27, 200.28, 201.15

[56] References Cited

U.S. PATENT DOCUMENTS

| | | | |
|---|---|---|---|
| 1,881,192 | 10/1932 | Hull | 128/201.15 |
| 2,971,196 | 2/1961 | Howell | 2/438 |
| 3,231,897 | 2/1966 | Woolfolk, Sr. | 2/438 |
| 3,434,882 | 3/1969 | Carolin | 134/102 X |
| 3,605,766 | 9/1971 | Carlani, Jr. | 2/438 X |
| 4,150,681 | 4/1979 | Howarth, Jr. | 134/172 |
| 4,369,782 | 1/1983 | McGee | 2/410 X |

FOREIGN PATENT DOCUMENTS

| | | | |
|---|---|---|---|
| 1098537 | 3/1955 | France | 128/200.27 |

*Primary Examiner*—Philip R. Coe
*Attorney, Agent, or Firm*—Fleit, Jacobson, Cohn & Price

[57] ABSTRACT

An upstanding helmet window panel has a pressurized fluid manifold extending along the upper margin of the window panel including longitudinally spaced spray jet outlet structure for spray discharging fluid from the manifold onto the upper margin of the window panel at an acute angle relatively thereto. A combination of cleaning liquid (water) and gas (air) is supplied to the manifold under pressure and the water and air are discharged from the jet outlet structures in a pulsating manner with the pulsating discharges of water serving to increase the cleaning action on the window panel and forming a layer of water flowing over the panel and the pulsating discharges of air serving to form a curtain of air over the layer of water on the window to smooth out and maintain a generally constant thickness of the water layer and thus increase visibility therethrough.

8 Claims, 2 Drawing Sheets

PULSATING WATER AND AIR JET STRUCTURE FOR CLEANING HELMET WINDOW

BACKGROUND OF THE INVENTION

1. Field of the Invention

The instant invention pertains to a series of pulsating fluid jets for directing fluids across the exterior surface of a helmet window, wherein the associated helmet is to be used in a dust laden atmosphere and the pulsating fluid jets function to maintain the exterior surface of the window clean of dust and form a reasonably constant flow of liquid across the window exterior surface and a flow or curtain of air thereover so as to maintain maximum visibility by a person wearing the associated helmet.

2. Description of Related Art

Various different forms of helmets and goggles including fluid jet structures for maintaining the exterior surface of a viewing window relatively clean heretofore have been provided. Examples of these previously known devices are disclosed in U.S. Pat. Nos. 1,881,192, 2,971,196, 3,231,897, 3,605,766, 4,150,681 and 4,369,782. However, these previously known devices are not particularly well adapted to function well in a heavily dust laden atmosphere such as that which is encountered by workmen operating dry or wet sand blasting equipment. Further, these previously known devices are not capable of maintaining maximum vision through the associated window while still providing a constant flow of cleaning liquid thereacross.

SUMMARY OF THE INSTANT INVENTION

The helmet window cleaning apparatus of the instant invention is used in conjunction with a helmet of the type into which ventilation and breathing air is constantly piped and the window cleaning apparatus utilizes a portion of the pressurized air source by which the interior of the helmet is ventilated and supplied breathing air for mixing with water or other cleaning liquid to pulse discharged in jet form onto and across the window surface to be maintained clean.

A portion of air under pressure supplied to the helmet for ventilation and breathing purposes is controllably, through an air adjusting valve, admitted into the inlet end of a cleaning fluid supply line in an intermediate length portion of which an eductor assembly is interposed. The eductor assembly is operatively connected to a supply of cleaning liquid such as water under pressure through a supply line equipped with a liquid flow adjusting valve disposed upstream from the eductor assembly and the outlet end of the cleaning fluid supply line opens into an elongated manifold having water and air jet outlets spaced longitudinally therealong, the manifold extending along the upper margin of the associated helmet window and the jet outlets are inclined approximately 20° relative to the window for pulse discharging jets of water and air under pressure from the manifold onto the window and downwardly thereacross.

Because the manifold is supplied air and water under pressure and the eductor assembly functions to admix the water and air in a manner such that the water includes bubbles of air therein when supplied to the manifold, the cleaning fluid comprising the combined water and air is discharged from the jet outlets in a pulsating manner. Since bubbles of air alone are being discharged from the plurality of jet outlets a curtain of air is formed over the water flowing downwardly across the window and has the effect of smoothing out the water layer flowing across the outer surface of the window so as to maintain maximum visibility for the wearer of the helmet, even though the window is constantly being bathed by a flow of water thereover.

The main object of this invention is to provide an apparatus by which the exterior surface of the window of a helmet may be continuously bathed and washed clean of any accumulation of dust tending to fall thereon.

Another object of this invention is to provide an apparatus which will, even though the window is being constantly cleansed by a flow of liquid such as water thereover, maintain maximum vision of the wearer of the helmet.

A further important object of this invention is to provide an apparatus in accordance with the preceding objects and which will also function to discharge cleaning fluids across the outer surface of a window to be cleaned in a pulsating manner.

An ancillary object of this invention is to provide an apparatus including controls therefor whereby the rate of water and air being supplied to the window cleaning apparatus may be independently varied and varied independently of the amount of ventilation and breathing air supplied to the interior of the associated helmet.

Yet another object of this invention is to provide an apparatus in accordance with the preceding objects and which may be readily adapted to existing types of helmets supplied with ventilation and breathing air merely by the addition of (1) a water supply line operably connected to a supply of water under pressure and including a flow controlling valve, (2) a cleaning fluid line equipped with an eductor operatively associated with the water supply line and including a flow control valve upstream from the eductor and appropriate connections to the ventilating and breathing air supply line.

A final object of this invention to be specifically enumerated herein is to provide an apparatus in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
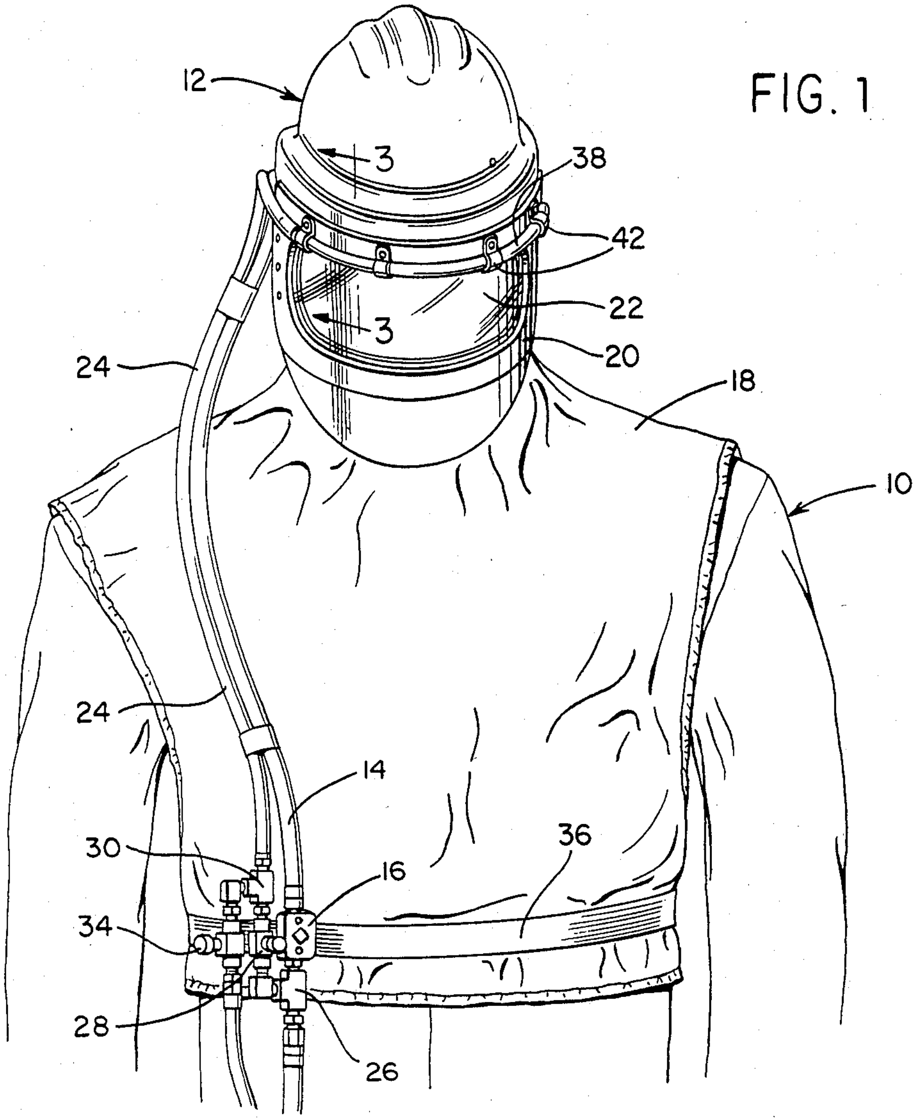
FIG. 1 is a front elevational view of a typical form of helmet used by a dry and wet sand blasting workman and with which the instant invention is operatively associated, the helmet also being operatively associated with a vest-type garment worn by the workman.
Figure 2:
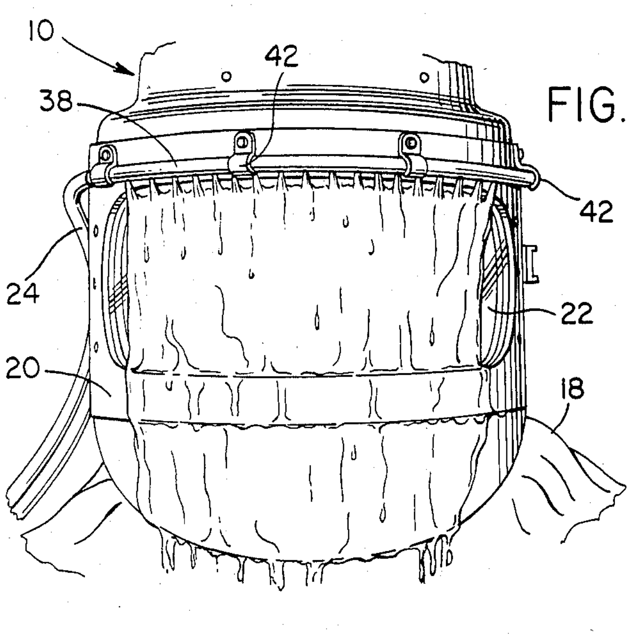
FIG. 2 is an enlarged front elevational view of the forward window portion of the helmet.

Referring now more specifically to the drawings, the numeral 10 generally designates a workman wearing a conventional helmet referred to in general by the reference numeral 12 and designed to provide ventilation and breathing air to the interior of the helmet.

Air under pressure is supplied to the interior of the helmet through an air supply line 14 to the inlet end of which air under pressure is supplied from any convenient source of compressed air. The line 14 includes an intermediate length air flow controlling valve 16 which may be controlled by the workman 10. The helmet 12 is operatively connected to a vest-type garment 18 from beneath which ventilation and breathing air exhausted from the helmet 12 is discharged. The forward portion of the helmet 12 include a face covering front wall 20 having a window 22 therein whereby the workmen 10 may view through the front wall 20 of the helmet 12.

The foregoing comprises a description of a conventional form of combined helmet and vest-type garment which is well known in the industry.

When the helmet 12 is utilized by a dry sandblasting workman, air entrained grit and other sand-blasting residue tends to collect on the exterior surface of the window. In addition, when a wet sand-blasting operation is being carried out, the exterior surface of the window 22 may be splattered with wet sand and wet sand-blasting residue. These occurrences, of course, severely limit the vision of the workmen 10 through the window 22. In addition, if such dry or wet sand and sand-blasting residue is to be removed from the exterior of the window, extreme care must be taken to prevent the window 22 from being scratched.

In order to maintain the exterior surface of the window 22 clean, a window cleaning fluid supply line 24 is provided and the inlet end thereof is communicated with the interior of the air supply line 14 through the utilization of a T-fitting 26. In addition, the inlet end of the cleaning fluid supply line 24 has an air flow controlling valve 28 serially connected therein as well as an eductor assembly 30. The eductor assembly is connected in the line 24 downstream from the valve 28 and the outlet end of a water supply line 32 opens laterally into the eductor assembly 30 and includes a water flow controlling valve 34 serially connected therein. All of the valves 16, 28 and 34 are supported from a waist encircling belt 36 worn by the workman 10 about the lower skirt portion of the vest-type garment 18.

Figure 3:
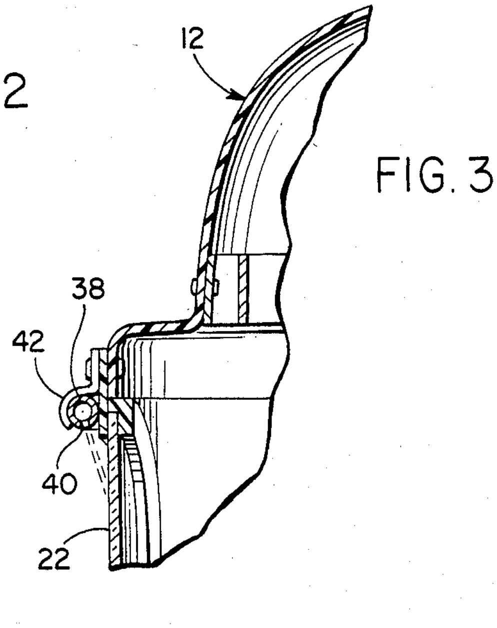
FIG. 3 is an enlarged fragmentary vertical sectional view taken substantially upon the plane indicated by the section line 3—3 of FIG. 1.
Figure 4:
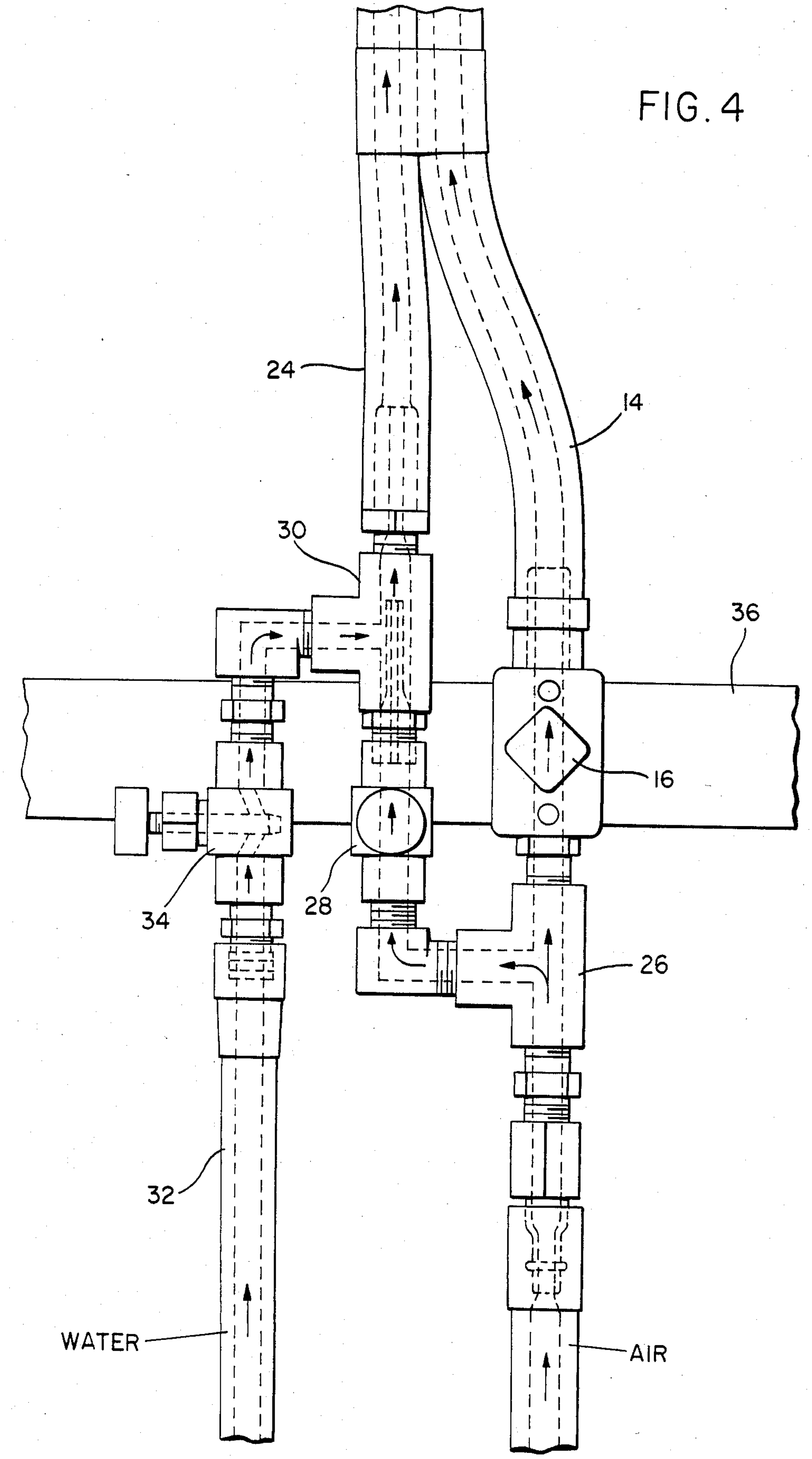
FIG. 4 is an enlarged fragmentary elevational view of the operative connection between the ventilation and breathing air supply line conventionally provided on the helmet and the helmet window cleaning fluid delivery structure.

The outlet end of the cleaning fluid supply line 24 incorporates an arcuate manifold 38 secured to the helmet 12 along that horizontal portion thereof defining the upper margin of the window 22 and includes longitudinally spaced fluid jet outlets 40 spaced longitudinally therealong, the manifold 38 being supported from the helmet 12 by a plurality of supportive clips 42. Further, the outlets 40 are oriented to discharge fluid jets therefrom downwardly upon the upper margin of the window 22 along paths inclined generally 20° relative to the window 22, see FIG. 3.

In operation, the vest-type garment and helmet 12 are placed on the workman 10 in the manner illustrated in FIG. 1 and the valve 16 is adjusted to supply the desired amount of ventilation and breathing air to the interior of the helmet 12. Then, the valves 28 and 34 are opened and adjusted to provide a mixture of air and water in the cleaning fluid supply line 24 which terminates in the manifold 38. Then, as the workman 10 is carrying out a dry or wet sand-blasting operation water and air are discharged in jet form from the jet outlets 40 downwardly onto the outer surface of the window 22 and flow downwardly thereover to prevent the accumulation of dry sand-blasting dust and debris or wet sand-blasting debris from collecting on the outer surface of the window 22.

Inasmuch as the cleaning fluid supply line and the manifold 38 have a mixture of water and air under pressure flowing therethrough, the fluid comprising the compressed air and water being discharged from the jet outlets 40 is discharged therefrom in pulses. Thus, a greater cleaning action is afforded the outer surface of the window 22. In addition, immediately after a pulse of water is discharged from each outlet 40 a quantity of air is discharged therefrom and the pulsating action is sufficiently rapid to enable the pulses of air being discharged from the jet outlets 40 to form a reasonably constant downward flow curtain of air over the layer of water or other cleaning liquid flowing downwardly over the outer surface of the window 22. This curtain of air serves to smooth out the layer of cleaning liquid flowing downwardly over the window 22 and results in better vision by the workman 10.

The valves 16, 28 and 34 may be adjusted as desired by the workman 10, according to the instant working conditions. Of course, if the workman is exerting more than usual physical energy, there will be a greater supply of ventilation and breathing air supplied to the interior of the helmet 12 through the air supply line 14. Under this condition, it may be necessary to open the valve 28 slightly in order to assure adequate quantities of air passing to the manifold 38 through the line 24 and the valve 34 also may need to be adjusted in order to maintain the proper air-to-water ratio flowing through the line 24.

The foregoing is considered as illustrative only of the principles of the invention. Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed as new is as follows:

1. A helmet including a forward facing window panel for forward viewing by a wearer of the helmet from therewithin and wherein the window panel includes at least one major dimension margin, a plurality of spray jet means supported from said helmet and spaced along said margin for discharging spray jets of fluid therefrom onto said margin at an acute angle thereon for directing the discharged fluid across said window panel toward the opposite margin thereof, means for supplying a fluid mixture comprising air and water under pressure to said spray jet means, said helmet including an air supply line to which air under pressure is supplied and which opens into the interior of said helmet for admitting ventilation and breathing air into the interior of said helmet.

2. The helmet of claim 1 wherein said one major dimension margin comprises an upper transverse margin of said window panel.

3. The helmet of claim 1 wherein said means for supplying a fluid mixture includes a cleaning liquid supply line and a cleaning fluid supply line, said cleaning fluid supply line including an inlet end opening into said air supply line and having an air flow control valve therein, and eductor assembly in said cleaning fluid supply line downstream from said air flow control valve, said cleaning liquid supply line including an inlet end to which cleaning liquid is supplied under pressure and an outlet end opening into said eductor assembly, said cleaning liquid supply line including a liquid flow control valve therein upstream from said eductor assembly, said cleaning fluid supply line being operatively connected with said spray jet means for supplying a mixture of cleaning liquid and air to said spray jet means.

4. The helmet of claim 3 wherein said air supply line includes an air flow controlling valve downstream from the point at which the inlet end of said cleaning fluid supply line opens into said air supply line.

5. The helmet of claim 3 wherein said outlet end of said cleaning fluid supply line incorporates a manifold extending along said one major dimension margin and said spray jet means are spaced along said manifold.

6. The helmet of claim 5 wherein said one major dimension margin comprises an upper transverse margin of said window panel.

7. The helmet of claim 6 wherein said spray jet means comprise jet outlet openings formed in and spaced along said manifold.

8. The helmet of claim 7 wherein said jet outlet openings open outwardly of said manifold toward said major dimension margin at an angle inclined generally 20° relative to the outer surface of said window panel.

* * * * *